United States Patent
Bergt et al.

(10) Patent No.: US 9,962,292 B2
(45) Date of Patent: May 8, 2018

(54) AFTER-TREATMENT OF REFRACTION CORRECTION BY OPHTHALMIC SURGERY

(75) Inventors: Michael Bergt, Weimar (DE); Carsten Lang, Eisenberg (DE)

(73) Assignee: Carl Zeiss Meditec AG, Jena (DE)

( * ) Notice: Subject to any disclaimer, the term of this patent is extended or adjusted under 35 U.S.C. 154(b) by 928 days.

(21) Appl. No.: 14/234,128

(22) PCT Filed: Jul. 20, 2012

(86) PCT No.: PCT/EP2012/064273
§ 371 (c)(1),
(2), (4) Date: Jan. 21, 2014

(87) PCT Pub. No.: WO2013/014072
PCT Pub. Date: Jan. 31, 2013

(65) Prior Publication Data
US 2014/0155875 A1     Jun. 5, 2014

(30) Foreign Application Priority Data

Jul. 22, 2011   (DE) .......................... 10 2011 108 645

(51) Int. Cl.
*A61F 9/008*     (2006.01)

(52) U.S. Cl.
CPC ...... *A61F 9/00836* (2013.01); *A61F 9/00827* (2013.01); *A61F 2009/00872* (2013.01); *A61F 2009/00897* (2013.01)

(58) Field of Classification Search
CPC .............. A61F 9/00827; A61F 9/00804; A61F 9/00836

USPC ................. 606/5, 4; 128/898; 351/206, 212; 607/89
See application file for complete search history.

(56) References Cited

U.S. PATENT DOCUMENTS

| | | | |
|---|---|---|---|
| 8,337,489 B2 * | 12/2012 | Donitzky | A61F 9/008 606/4 |
| 8,597,283 B2 | 12/2013 | Bischoff et al. | |
| 8,623,038 B2 | 1/2014 | Bischoff et al. | |
| 2008/0275433 A1 * | 11/2008 | Russmann | A61F 9/008 606/5 |
| 2008/0319428 A1 * | 12/2008 | Wiechmann | A61F 9/008 606/5 |

(Continued)

FOREIGN PATENT DOCUMENTS

| | | |
|---|---|---|
| DE | 10 2007 019 814 A1 | 10/2008 |
| DE | 10 2007 019 815 A1 | 10/2008 |

(Continued)

*Primary Examiner* — Gary Jackson
*Assistant Examiner* — Zahed Kabir
(74) *Attorney, Agent, or Firm* — Christensen, Fonder, Dardi & Herbert PLLC

(57) ABSTRACT

A planning system for generating control data, a treatment device for ophthalmic surgery to correct refraction, and a method for generating control data for such a treatment device, the method enabling easy continuation of an interrupted treatment or correction of a previous treatment. To this end, the planning system has a calculating device configured to define a corneal incision surface, wherein the calculating device determines the new corneal incision surface such that the existing corneal incision surface is incised by at least a part of the new corneal incision surface at an angle of between 60° and 120°.

18 Claims, 5 Drawing Sheets

(56) References Cited

U.S. PATENT DOCUMENTS

| | | | | |
|---|---|---|---|---|
| 2010/0049174 A1* | 2/2010 | Kuehnert | ............... | A61F 9/008 606/4 |
| 2010/0087802 A1 | 4/2010 | Bischoff et al. | | |
| 2010/0241108 A1* | 9/2010 | Wullner | ................. | A61F 9/008 606/5 |
| 2010/0331830 A1* | 12/2010 | Bischoff | ................. | A61F 9/008 606/5 |
| 2010/0331831 A1 | 12/2010 | Bischoff et al. | | |
| 2011/0040293 A1* | 2/2011 | Bor | ......................... | A61F 9/008 606/5 |
| 2014/0107631 A1* | 4/2014 | Ferrari | ................... | A61F 9/013 606/5 |

FOREIGN PATENT DOCUMENTS

| | | | | |
|---|---|---|---|---|
| DE | 102007019814 A1 * | 10/2008 | ............. | A61F 9/008 |
| DE | 10 2007 053 281 A1 | 5/2009 | | |
| DE | 10 2007 053 283 A1 | 5/2009 | | |
| DE | 10 2008 056 488 A1 | 5/2010 | | |
| EP | 0 754 103 B1 | 11/1997 | | |

* cited by examiner

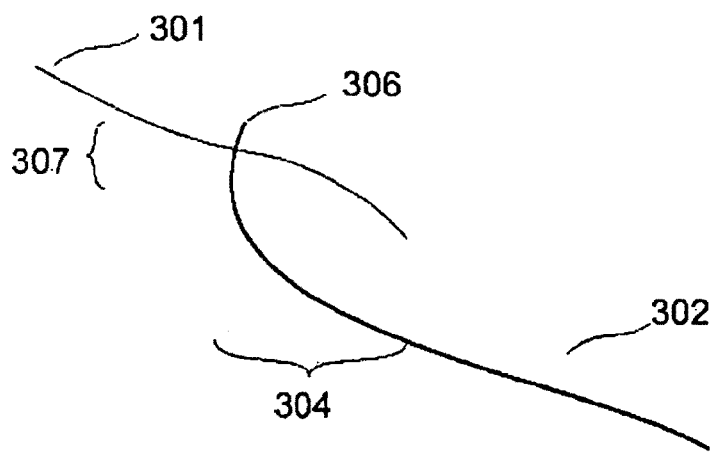
Fig. 8d
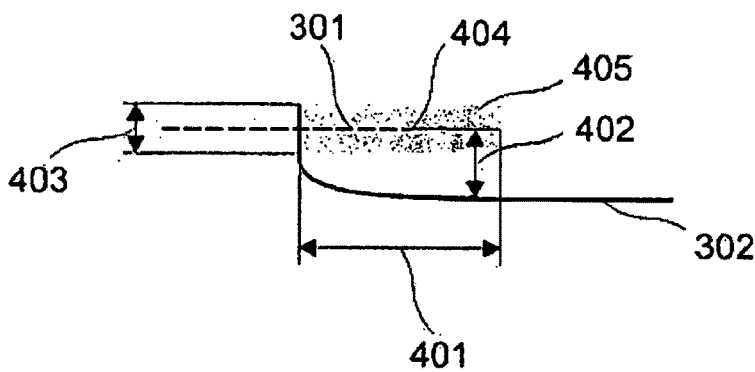
Fig. 9
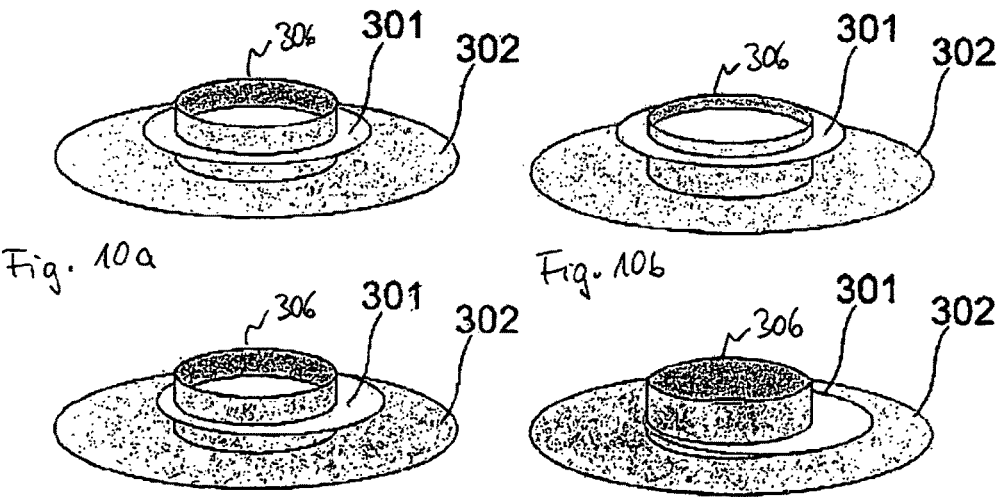
Fig. 10a    Fig. 10b
Fig. 10c    Fig. 10d

AFTER-TREATMENT OF REFRACTION CORRECTION BY OPHTHALMIC SURGERY

PRIORITY CLAIM

The present application is a National Phase entry of PCT Application No. PCT/EP2012/064273, filed Jul. 20, 2012, which claims priority from German Application Number 102011108645.9, filed Jul. 22, 2011, the disclosures of which are hereby incorporated by reference herein in their entirety.

FIELD OF THE INVENTION

The invention relates to a planning device for generating control data for a treatment apparatus that cuts at least one incision surface in the cornea, by means of a laser device. The invention furthermore relates to a treatment apparatus that has a planning device of the stated type. The invention furthermore relates to a method for generating control data for a treatment apparatus that cuts at least one incision surface in the cornea by means of a laser device. Finally, the invention also relates to a method for ophthalmic surgery, wherein at least one incision surface in the cornea is cut with a laser device, by means of a treatment apparatus.

BACKGROUND OF THE INVENTION

In the state of the art, different treatment methods having the goal of refraction correction of the human eye are known. In this connection, it is the goal of the operation methods to modify the cornea in a targeted manner in order to thereby influence the refraction of light. Multiple operation methods are used for this purpose. Currently the most widespread method is what is called laser in-situ keratomileusis, also abbreviated as LASIK. In this connection, first a cornea flap is detached from the cornea surface on one side, and folded over to the side. Detaching of this flap can take place by means of a mechanical microkeratome or also by means of what is called a laser keratome, such as that sold by Intralase Corp., Irvine, USA, for example. After the flap has been detached and folded to the side, use of an excimer laser that wears away the corneal tissue thereby exposed under the flap, by means of ablation, is provided during the LASIK operation. After the volume that lies below the cornea surface has been evaporated in this manner, the cornea flap is folded back into its original position.

Use of a laser keratome for freeing the flap is advantageous, as compared with a mechanical blade, because the risk of infection is reduced and, at the same time, the incision quality is improved. In particular, the flap can be produced with a much more constant thickness if laser radiation is used. Also, the incision is generally smoother, and this reduces the risk of subsequent optical disturbances caused by the boundary surface that remains even after the operation. However, it is a disadvantage of this method that two different treatment apparatuses have to be used, for one thing, specifically, the laser keratome for detaching the flap, and for another, the laser that evaporates the corneal tissue.

These disadvantages are eliminated in a method that was recently implemented by Carl Zeiss Meditec AG and is abbreviated with the designation FLEX. In this method, an incision geometry is formed in the cornea of the eye by means of a femtosecond laser, which separates a cornea volume (called a lenticule) in the cornea. This is then manually removed by the operator, after the flap that covers the lenticule has been folded to the side. The advantage of this method lies, for one thing, in that the incision quality is improved once again by means of the use of the femtosecond laser.

For another thing, the eximer laser is no longer used, and only one treatment apparatus is required.

An expansion of the FLEX method is the SMILE method, in which the separated lenticule is removed through a small opening incision, and thereby the flap incision of the FLEX method can be eliminated.

In the production of incision surfaces in the cornea by means of laser radiation, the optical radiation effect is usually utilized in that an optical perforation is produced. Also, it is known to introduce individual pulses, the energy of which lies below a threshold value for an optical perforation, into the tissue or material in such a covered manner that material or tissue separation is achieved in this way, as well. This concept of incision production in the corneal tissue allows a great variety of incisions.

In the laser surgery operation methods described, an incision remains in the cornea as the result of the treatment. The incision is no longer visible with the naked eye after a short time, but never heals, due to the particular nature of the cornea of the eye, because in this regard, the cornea of the eye is "dead" tissue. The tissue parts above an incision are no longer firmly connected with the tissue parts below the incision, because of the incision.

However, a need for after-treatment can occur, specifically if the result of the previous operation is not yet satisfactory with regard to the refraction correction, or if the previous operation could not be sufficiently concluded for some reason (for example due to discontinuation of the operation).

In the event of an insufficient refractory correction, it is known, for the excimer-laser-based LASIK operation, to lift the cornea flap up once again for the after-treatment, and to remove further corneal tissue by ablation.

However, this approach cannot be used for the FLEX method, because the incision in the cornea from the first treatment is not easily accessible or evident. The flap would have to be folded up again in order to remove the material that lies underneath, and the femtosecond laser is not intended for this; further work would have to be performed using an excimer laser. This approach also cannot be implemented in the SMILE method, because the incision from the first treatment, which runs in the interior of the cornea, is no longer accessible or evident.

The same holds true for an interrupted laser-based operation.

A first solution for this problem is described in DE 10 2007 019814. In this solution a planning device that has an interface for supplying cornea data that contain information about pre-operative steps generated in a previous ophthalmic surgery operation, and has calculation means for establishing a cornea incision surface that delimits the cornea volume to be removed, where the calculation means establish the cornea incision surface on the basis of the cornea data and generate a control data set for controlling the laser device for the cornea incision surface.

With the solution described there, however, it is not ensured that further treatment will take place at the desired location, because displacements or rotations of the eye can occur between the completion of the first treatment and its resumption or continuation. In order to avoid this problem, it is proposed, in DE 102007019814, to place the new incision(s) in such a manner that they are guaranteed not to intersect the original incisions, i.e., either completely posterior or completely anterior to the original incision.

This cannot always be implemented, because of the geometry and, in particular, the required stability of the cornea.

In DE 10 2008 056 488, it is therefore proposed to determine the original incision by means of a special detector. OCT (optical coherence tomography) or a confocal detector are disclosed as suitable detectors. Therefore this solution requires significant effort/expenditure for the additional detector.

SUMMARY OF THE INVENTION

The claimed invention is therefore based on the task of indicating a planning device for generating control data, a treatment apparatus for refraction-correcting ophthalmic surgery, and a method for generating control data for such a treatment apparatus, with which continuation of interrupted treatment or correction of a previous treatment is easily possible.

This task is accomplished, according to an embodiment of the invention, with a planning device of the type stated initially, which has calculation means for establishing a cornea incision surface, where the calculation means determine the new cornea incision surface in such a manner that the existing cornea incision surface is intersected by at least a part of the new cornea incision surface at an angle between 60° and 120°, preferably 80° to 100°, particularly preferably about 90°.

The invention is furthermore accomplished with a treatment apparatus that has a laser device that cuts at least one incision surface in the cornea by means of laser radiation in accordance with control data, and a planning device according to the type just mentioned for generating the control data, wherein the planning device determines the new cornea incision surface in such a manner that the existing cornea incision surface is intersected by at least a part of the new cornea incision surface at an angle between 60° and 120°, preferably 80° to 100°, particularly preferably about 90°.

Finally, an embodiment of the invention is also accomplished with a method for generating control data in accordance with the type stated initially, which includes: establishing a cornea incision surface, generating a control data set for the cornea incision surface for controlling the laser device, wherein the planning device determines the new cornea incision surface in such a manner that the existing cornea incision surface is intersected by at least a part of the new cornea incision surface at an angle between 60° and 120°, preferably 80° to 100°, particularly preferably about 90°.

Finally, the invention may also be accomplished with a method that comprises: establishing a cornea incision surface, generating a control data set for the cornea incision surface, transferring the control data to the treatment apparatus, and generating the incision surfaces by controlling the laser device with the control data set, wherein the new cornea incision surface is determined in such a manner, when generating the control data set, that the existing cornea incision surface is intersected by at least a part of the new cornea incision surface at an angle between 60° and 120°, preferably 80° to 100°, particularly preferably about 90°.

Of course, planning the cornea incision surface has particular importance in the event of a continuation, because the already existing incisions must be taken into consideration.

A continuation is possible all the more simply or precisely, the more precise the knowledge about the steps already implemented at interruption. For this reason, it is fundamentally advantageous, independent of the implementation of the after-treatment, if a laser surgery treatment apparatus for refractive ophthalmic surgery has a device that records the progression of the steps generated during an operation. If the treatment apparatus works with pulsed laser radiation, the record preferably comprises the position and energy of each laser radiation pulse focused into the cornea. This great data recording effort proves to be advantageous if after-treatment is necessary, particularly in the event of an operation that was not performed completely. Then, continuation of the interrupted production of the incision surface is possible in a simple and precise manner.

For this purpose, it is possible to use the already existing incision and to establish the cornea incision surface in such a manner that it supplements or makes use of this incision. In this way, faster production of the incision surface is achieved, but more precise knowledge about the existing incision is required.

In the case of continuation of an operation that was not completed properly, there is always the problem that depending on how the incision was produced, possibly only incomplete incision surfaces are present.

For example, a lenticule incision that was supposed to delimit the cornea volume that was supposed to be removed during the previous operation, in the posterior direction, might have been performed completely or partially. Possibly, a partial or even an almost complete flap incision also exists, which was supposed to delimit the lenticule in the anterior direction. A case can even occur in which the edge incision, which then allows the cornea flap to be folded away, is the only incision that was not yet completely performed. In every case, it is appropriate to continue the steps if it is known precisely what steps have been taken. In this connection, continuation can also include that the incision surface partly contains the incision already made, i.e., that after-treatment starts with producing the incision surface in a region in which a pre-operative incision is already expected. An overlap ensures continuous tissue cutting, in an interaction of the existing incision and the supplemental incision surface.

As the explanations regarding continuation make evident, the most precise positioning possible of the cornea incision surface and the position determination of the existing incision have great importance. In this connection, the following method of procedure is advantageous:

Recording of the point in time when the operation was stopped brings with it simplification and an increase in the reliability of the record. It is therefore advantageous to simplify recording to the effect that it is not the position of every laser radiation pulse emitted into the cornea that is recorded, but rather merely parameters of the laser pulse emission (e.g., frequency of the pulses), deflection of the focus (e.g., deflection speed), and the precise time statement of a possible discontinuation of the operation and incision geometry information.

In this way, not only information about the course of the incision previously implemented, but also geometric information about the location of this incision course, with current geometric assignment of the treatment device to the eye is available, so that a displacement and/or rotation of the eye between the original treatment and its continuation can be taken into consideration when establishing the control data set.

It is understood that the characteristics mentioned above and those still to be explained below can be used not only in the given combinations but also in other combinations or by themselves, without departing from the scope of the present invention.

BRIEF DESCRIPTION OF THE DRAWINGS

In the following, the invention will be explained in further detail, as an example, using the attached drawings, which also disclose characteristics essential to the invention, in which:

FIG. 9 is a schematic representation of tolerances that occur; and

FIG. 10 is a 3D schematic representations of different incision conditions, according to the present invention.

DETAILED DESCRIPTION

Figure 1:
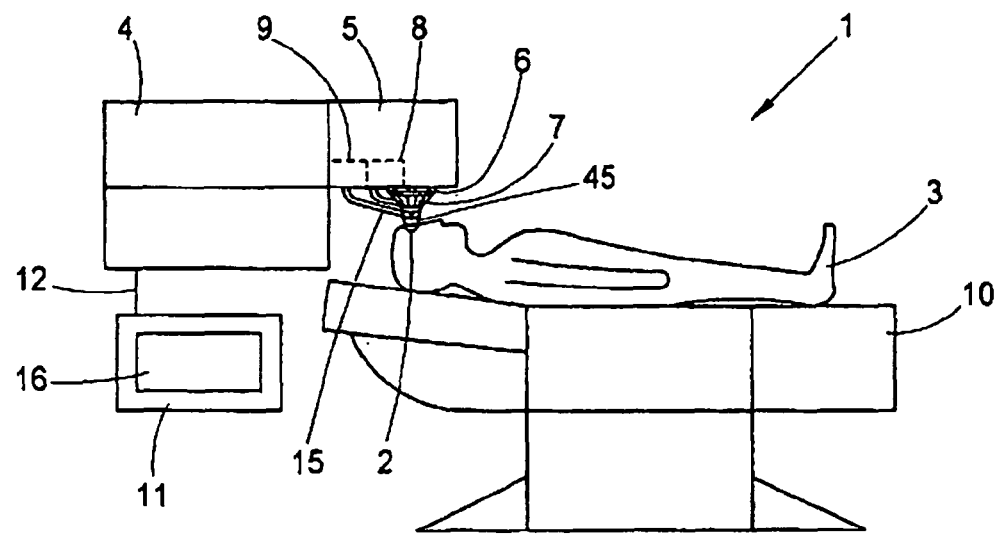
FIG. 1 is a schematic representation of a treatment apparatus having a planning device for after-treatment of an ophthalmic surgery refraction correction according to an embodiment of the invention.

A treatment apparatus for ophthalmic surgery is shown in FIG. 1 and provided with the general reference symbol 1. The treatment apparatus 1 is configured for introducing laser incisions into an eye 2 of a patient 3. For this purpose, the treatment apparatus 1 has a laser device 4 that emits a laser beam 6 from a laser source 5, the beam being directed into the eye 2, or into the cornea of the eye, respectively, as a focused beam 7. In an embodiment, the laser beam 6 is a pulsed laser beam having a wavelength between 400 nanometers and 10 micrometers. Furthermore, in an embodiment, the pulse length of the laser beam 6 lies in the range between 1 femtosecond and 10 picoseconds, where pulse repetition rates of 1 to 1000 kilohertz and pulse energies between 0.1 microjoules and 0.01 millijoules are possible. The treatment apparatus 1 thus produces an incision surface in the cornea of the eye 2, by means of deflection of the pulsed laser radiation. Therefore, a scanner 8 and a radiation intensity modulator 9 may also be provided in the laser device 4 or its laser source 5, respectively, for this purpose.

The patient 3 is situated on a couch 10 that is adjustable in three spatial directions, in order to align the eye correctly with regard to the incidence of the laser beam 6. In a preferred construction, the couch 10 is adjustable by means of a motor.

Control can particularly take place by means of a control device 11, which fundamentally controls the operation of the treatment apparatus 1 and is connected with the treatment apparatus by way of suitable data lines, for example connection lines 12, for this purpose. Of course, this communication can also take place in a different way, for example, by way of light conductors or wireless, for example. The control device 11 undertakes the corresponding adjustments and time controls of the treatment apparatus 1, particularly of the laser device 4, and thereby brings about corresponding functions of the treatment apparatus 1.

The treatment apparatus 1 furthermore has a fixation device 15 that fixes the cornea of the eye 2 in place with regard to the laser device 4. In this connection, the fixation device 15 can comprise a known contact lens 45 against which the cornea of the eye is placed by means of a partial vacuum, and which imparts a desired geometric shape to the cornea of the eye. Such contact lenses are known to a person skilled in the art, for example from DE 102005040338 A1. The disclosure content of DE 102005040338 A1 is incorporated by reference herein, to its full extent, to the extent that the description of a design of the contact lens 45 that is possible for the treatment apparatus 1 is involved.

The treatment apparatus 1 furthermore has a camera, not depicted, which can take a picture of the cornea 17 of the eye through the contact lens 45. In this connection, the illumination for the camera can be provided not only in the visible range, but also in the infrared range of light.

The control device 11 of the treatment apparatus 1 furthermore has a planning device 16 that will be explained in greater detail below.

Figure 2:
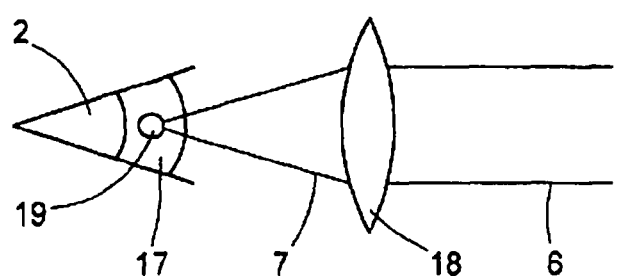
FIG. 2 is a schematic representation of the effect of the laser radiation that is used in the treatment apparatus of FIG. 1.

FIG. 2 schematically shows the method of effect of the incident laser beam 6. The laser beam 6 is focused and falls onto the cornea 17 of the eye 2 as a focused laser beam 7. For focusing, a lens 18 shown schematically is provided. It brings about a focus in the cornea 17, in that the laser radiation energy density is so great that a non-linear effect occurs in the cornea 17 in combination with the pulse length of the pulsed laser radiation 6. For example, each pulse of the pulsed laser radiation 6 can produce an optical perforation in the cornea 17 of the eye, which in turn initiates a plasma bubble indicated only schematically in FIG. 2. When the plasma bubble occurs, the tissue layer separation comprises a larger area than the focus 19, although the conditions for production of the optical perforation are achieved only in the focus 19. In order for an optical perforation to be generated by every laser pulse, the energy density, i.e., the fluence of the laser radiation, must lie above a specific, pulse-length-dependent threshold value. This relationship is known to a person skilled in the art, for example from DE 69500997 T1. Alternatively, a tissue-separating effect can also be achieved by means of pulsed laser radiation, in that multiple laser radiation pulses are emitted in an area where the focus spots overlap. Then, multiple laser radiation pulses work together in order to achieve a tissue-separating effect. However, the method of tissue separation that the treatment apparatus 1 uses is not of further relevance for the following description; the only essential thing is that production of an incision surface takes place in the cornea 17 of the eye 2.

In order to perform an ophthalmic surgery refraction correction, a cornea volume is removed from an area within the cornea 17 by means of the laser radiation 6, in that tissue layers are cut there, which isolate the cornea volume and then allow its removal. To isolate the cornea volume to be removed, in the case of laser radiation introduced in a pulsed manner, for example, the position of the focus 19 of the focused laser radiation 7 in the cornea 19 is adjusted.

Figure 3:
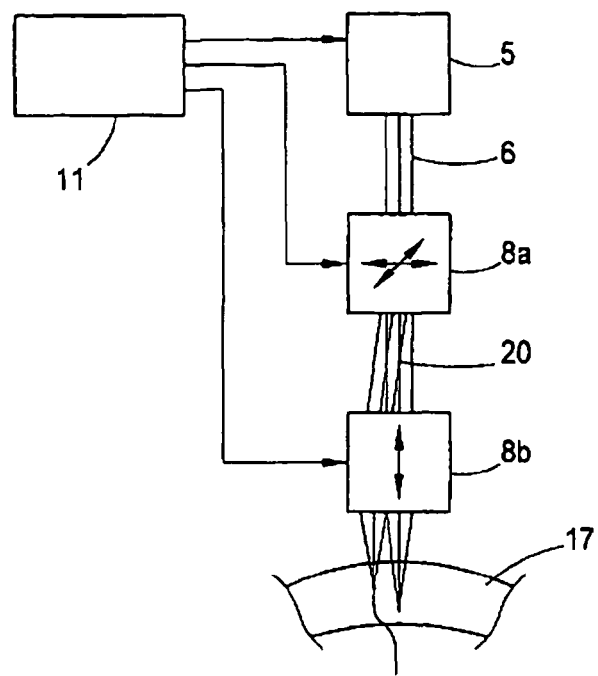
FIG. 3 is a further schematic representation of the treatment apparatus of FIG. 1, with regard to introduction of the laser radiation.

This is shown schematically in FIG. 3. The refraction properties of the cornea 17 are modified in a targeted manner by means of removal of the volume, in order to thereby achieve the refraction correction. The volume is therefore generally lens-shaped and is referred to as a lenticule.

In FIG. 3, the elements of the treatment apparatus 1 are entered only to the extent that they are required for an understanding of the production of the incision surface. As has already been mentioned, the laser beam 6 is bundled in a focus 19 in the cornea 17, and the position of the focus 19 in the cornea is adjusted, so that focusing energy from laser radiation pulses is introduced into the tissue of the cornea 17 at different locations to produce the incision surface. The laser radiation 6 is made available by the laser source 5, preferably as pulsed radiation. The scanner 8 is structured in two parts in the construction of FIG. 3, and consists of an xy scanner 8a that is implemented, in one variant, by two galvanometer mirrors that deflect essentially orthogonally. The scanner 8a deflects the laser beam 6 coming from the laser source 5 in two dimensions, so that after the scanner 9, a deflected laser beam 20 is present. The scanner 8a thereby brings about an adjustment of the location of the focus 19 essentially perpendicular to the main incidence direction of the laser beam 6 in the cornea 17. To adjust the depth position, a z scanner 8b, which is configured as an adjustable telescope, for example, is also provided in the scanner 8, in addition to the xy scanner 8a. The z scanner ensures that the z position of the location of the focus 19, i.e., its position on the optical axis of incidence, is changed. The z scanner 8b can follow or precede the xy scanner 8a.

Assignment of the individual coordinates to the spatial directions is not essential for the functional principle of the treatment apparatus 1, nor is it essential that the scanner 8a deflect about axes that are at right angles to one another. Instead, any scanner can be used that is able to adjust the focus 19 in a plane in which the incidence axis of the optical radiation does not lie. Furthermore, any desired non-Cartesian coordinate systems can be used for deflection or control of the location of the focus 19. Examples of these are spherical coordinates or cylindrical coordinates.

Control of the location of the focus 19 takes place by means of the scanners 8a, 8b, being controlled by the control device 11, which undertakes corresponding adjustments in the laser source 5, the modulator 9 (not shown in FIG. 3), as well as the scanner 8. The control device 11 ensures suitable operation of the laser source 5 as well as of the three-dimensional focus adjustment shown as an example here, so that ultimately, an incision surface that isolates a specific cornea volume that is to be removed for refraction correction is formed.

The control device 11 works according to predetermined control data that are predetermined as target points for the focus adjustment in the laser device 4, described merely as an example here, for example. The control data are generally compiled in a control data set. This results in geometric default values for the incision surface to be configured, for example the coordinates of the target points as a pattern. In this embodiment, the control data set then also contains concrete position values for the focus location adjustment mechanism, for example for the scanner 8.

Figure 4:
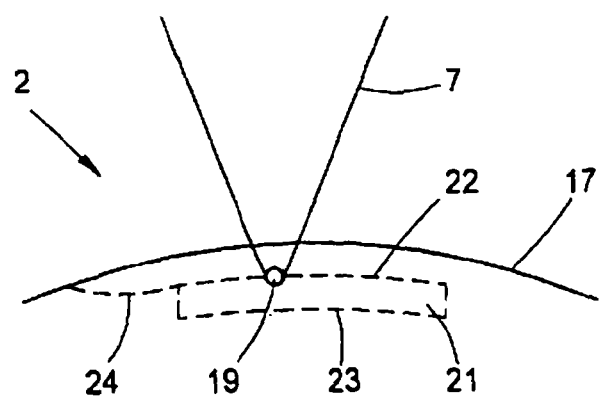
FIG. 4 is a schematic, sectional representation through the cornea of the eye, to illustrate removal of the cornea volume in connection with the ophthalmic surgery refraction correction.

Production of the incision surface, using the treatment apparatus 1, is shown in FIG. 4 as an example. A cornea volume 21 in the cornea 17 is isolated by means of adjustment of the focus 19 in which the focused beam 7 is bundled. For this purpose, incision surfaces are formed that are configured here, as examples, as an anterior flap incision surface 22 and as a posterior lenticule incision surface 23. These terms should merely be understood as examples here, and are supposed to establish the connection with the conventional Lasik or Flex method, for which the treatment apparatus 1 is also configured, as has already been explained. The only essential thing here is that the incision surfaces 22 and 23, as well as edge incisions not designated in any detail here, which bring the incision surfaces 22 and 23 together at their edges, isolate the cornea volume 21. Furthermore, a cornea flap that delimits the cornea volume 21 in the anterior direction can be folded away through an opening incision 24, so that the cornea volume 21 can be removed.

Alternatively, the SMILE method can be used, in which the cornea volume 21 is removed through a small opening incision, as described in DE 10 2007 019813 A1. The disclosure content of this document is incorporated here, to its full extent.

Figure 5:
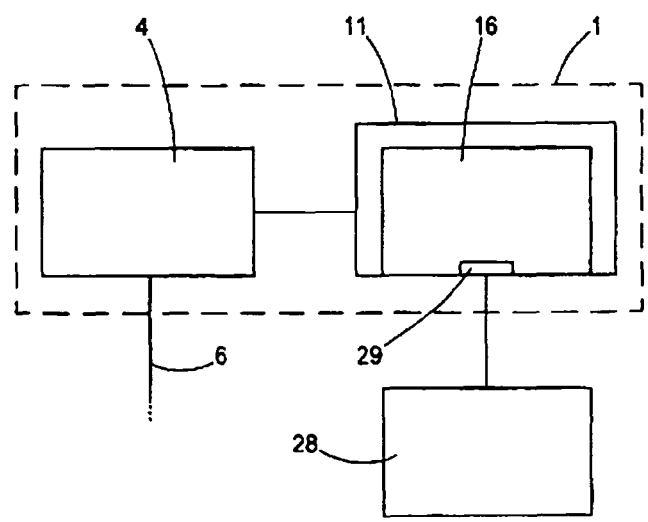
FIG. 5 is a schematic representation with regard to the structure of the treatment device of FIG. 1, with special reference to the planning device present there.

FIG. 5 schematically shows the treatment apparatus 1, and the importance of the planning device 16 will be explained in greater detail here, using this figure. In this variant, the treatment apparatus 1 has at least two devices or modules. The laser device 4 already described emits the laser beam 6 to the eye 2. In this connection, operation of the laser device 4 takes place, as has already been described, fully automatically by means of the control device 11, i.e. the laser device 4 starts generating and deflecting the laser beam 6 in response to a corresponding start signal, and in this connection produces incision surfaces that are structured in the manner described. The laser device 4 receives control signals from the control device 11, which previously had the corresponding control data made available to it. This takes place by means of the planning device 16, which is shown in FIG. 5 merely as an example, as a component of the control device 11. Of course, the planning device 16 can also be configured in a stand-alone manner and can communicate with the control device 11 in a wired or wireless manner. Then, the only essential thing is that a corresponding data transmission channel is provided between the planning device 16 and the control device 11.

The planning device 16 generates a control data set that is made available to the control device 11 for carrying out the ophthalmic surgery refraction correction. In this connection, the planning device utilizes measurement data concerning the cornea of the eye. In the embodiment described herein, these data come from a measurement device 28 that has measured the eye 2 of the patient 3 previously. Of course, the measurement device 28 can be configured, and can transmit the corresponding data to the interface 29 of the planning device 16, in any desired manner.

The planning device now supports the operator of the treatment apparatus 1 in establishing the incision surface for isolation of the cornea volume 21. This can go as far as fully automatic determination of the incision surfaces, which can be brought about, for example, in that the planning device 16 determines the cornea volume, the delimitation surfaces of which are defined as incision surfaces, from the measurement data, and generates corresponding control data for the control device 11 from this. At the other end of the degree of automation, the planning device 16 can provide input possibilities where a user enters the incision surfaces in the form of geometric parameters, etc. Intermediate steps provide suggestions for the incision surfaces, which the planning device 16 generates automatically and which can then be modified by a user. Fundamentally, all those concepts that were already explained in the above more general description part can be used here in the planning device 16.

In order to perform continuation of treatment, the planning device 16 generates control data for production of the incision surfaces, which data are then used in the treatment apparatus 1.

Figure 6:
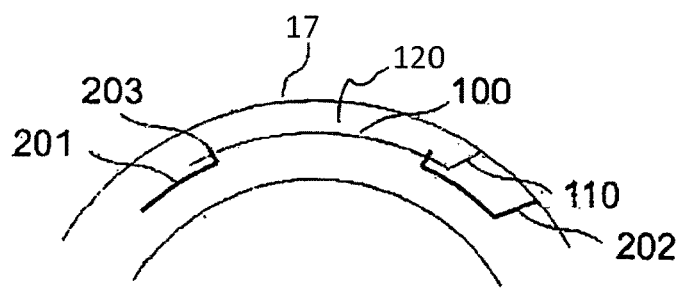
FIG. 6 is a schematic representation of a cornea cross-section.

FIG. 6 shows a schematic representation of a cornea cross-section to illustrate the geometric conditions described below. The cornea 17 has an existing flap incision 100 having an existing opening incision 110. The continuation incision consists of a ring-shaped flap incision 201 with a lateral incision 202 and a connecting mantle incision 203 that connects the incision 201 with the existing incision 100. In this connection, the lateral incision 202 is not complete, but rather has a gap that forms the hinge, in order to continue to hold the flap 120 that forms on the cornea 17.

Figure 7A:
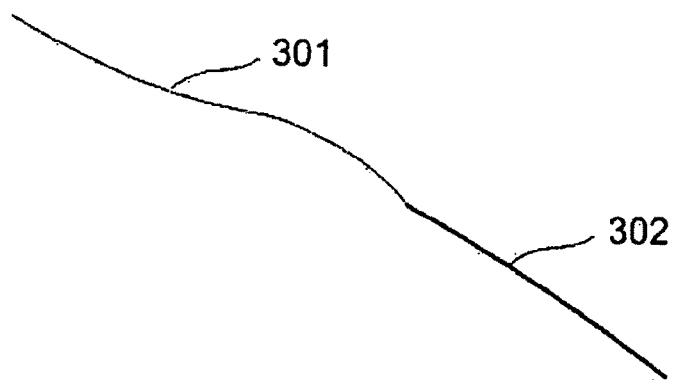
FIG. 7 is a schematic representation of different incision conditions according to the state of the art.
Figure 7B:
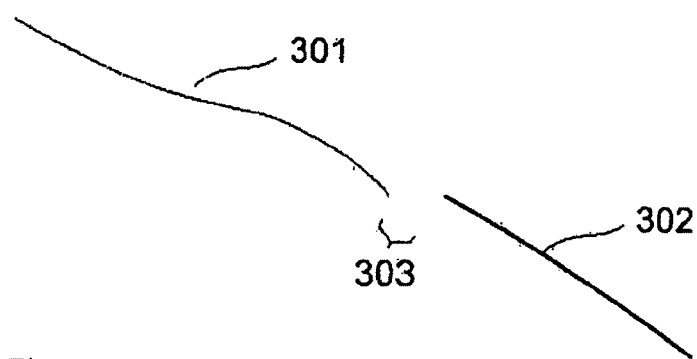
Figure 7C:
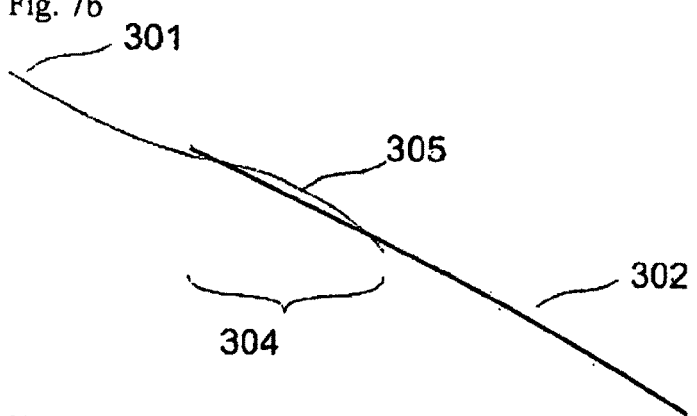

FIG. 7 shows a schematic representation of different incision conditions according to the state of the art. In FIG. 7a, the ideal case is shown: the expansion incision 202 follows the existing incision 301 without any gap. In reality, this will never succeed, if only due to tolerances that occur. Thus, FIG. 7b shows the case that a gap 303 occurs between the existing incision 301 and the expansion incision 302; the corneal tissue is not cut correctly. In FIG. 7c, the case is shown that the existing incision 301 and the expansion incision 302 overlap. In this connection, an undesirably separated piece of tissue 305 occurs in the overlap region 304, which puts the success of the operation in doubt if removed, because the calculated intended shape of the cornea cannot be achieved if this additional tissue is removed.

Figure 8A:
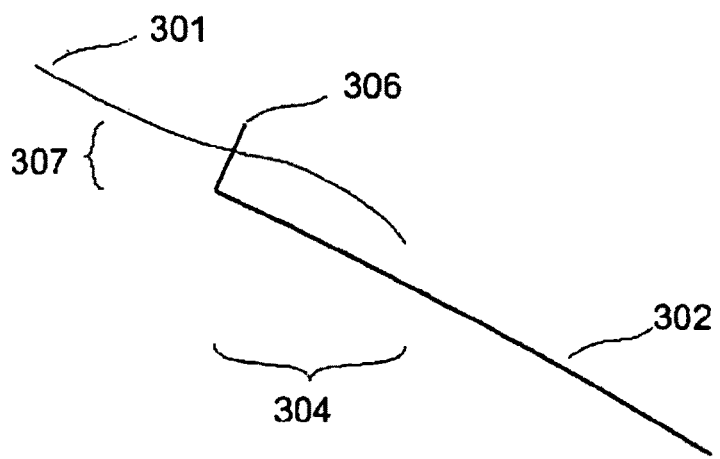
FIG. 8 is a schematic representation of different incision conditions according to an embodiment of the present invention.
Figure 8B:
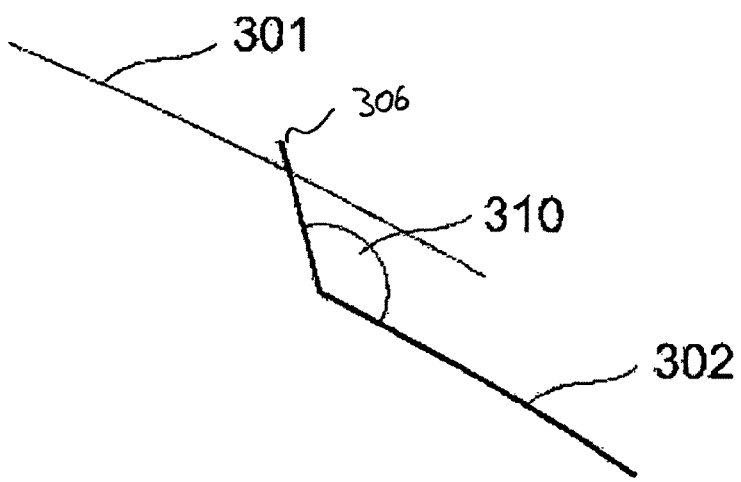
Figure 8C:
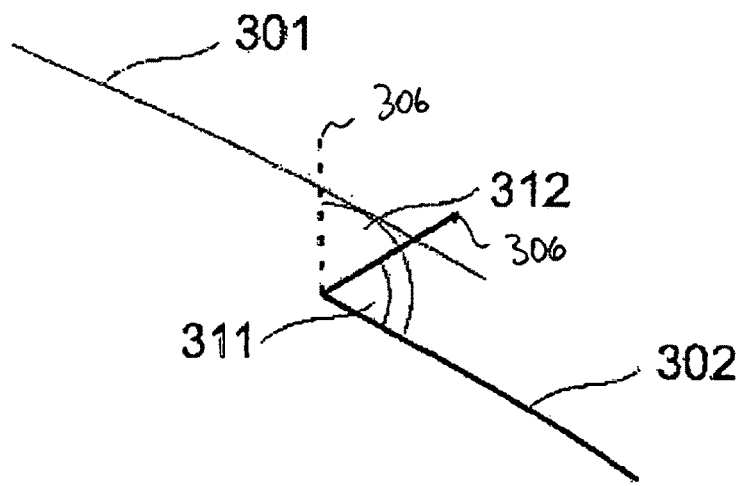

FIG. 8 shows a schematic representation of different incision conditions according to the present invention. In FIG. 8a, the particularly preferred conditions are shown: the expansion incision 302 has an overlap 304 with the existing incision 301, but is positioned deeper than the existing incision 301 by a tolerance range 307. The connection between the two incisions 301 and 302 is produced by means of a connecting incision 306, which is structured here as a mantle incision with an angle of 90° relative to the existing incision 301, where the incision 306 penetrates the existing incision 301 here and in the following, and goes beyond it. In this way, it is ensured that the two incisions 301 and 302 are connected without any undesirable tissue separation taking place as in FIG. 7. In FIG. 8b, it is shown that the mantle incision 306 can also take place at an angle 310 relative to the existing incision that is different from 90°. Here, ranges from 30° to 150° have proven to be suitable. In FIG. 8c, the angles 60° (311) and 120° (312) between existing incision 301 and continuation incision 302 are shown together, but in reality, always only one of these can be selected. In FIG. 8d, it is shown that the mantle incision 306 can also be structured as a curved incision.

FIG. 9 shows a schematic representation of the tolerances taken into consideration in guidance of the incisions. In order to reliably intersect the existing incision 301, the expansion incision 302 is extended in length by a vertical overlap region 403. So that no undesirable tissue separation occurs, a minimum distance 402 is maintained between the incisions 301 and 302. In order to intersect the original incision 301 reliably with the expansion incision 302, even if its location is not precisely known, a horizontal overlap region 401 is maintained. In this connection, the following values have proven to be suitable:

Horizontal overlap region 401: 10 μm-500 μm
Vertical overlap region 403: 10 μm-50 μm
Minimum distance 402: >403/2

FIG. 10 shows 3D schematic representations of different incision conditions according to the present invention. In FIG. 10a, optimal conditions are shown: the existing incision 301 and the expansion incision 302 are concentric; the mantle incision 306 securely connects the two. FIG. 10b shows a vertical offset between the real and the expected position of the existing incision 301; nevertheless, a secure connection with the expansion incision 302 is produced by means of the overlap 403 of the mantle incision (see FIG. 9). FIG. 10c shows a lateral offset between the real and the expected position of the existing incision 301; nevertheless, the horizontal overlap 401 (see FIG. 9) ensures that a secure connection with the expansion incision is produced. FIG. 10d shows the result when horizontal and vertical offset are present at the same time; here, too, a secure connection is produced without any undesirable separation of tissue coming about.

In general, the invention can be summarized as follows: If an incision to be made is supposed to be connected with an existing incision, and in this connection, positioning tolerances of the new incision relative to the old one must be accommodated and regions of an undefined double incision course are supposed to be avoided, the incisions must be formed in such a manner that they penetrate the existing incision at an angle of optimally 90°. In particular, if an existing incision is supposed to be expanded in the same direction, the new incision is intentionally offset relative to the existing one in order to produce an overlap region, and the connection is produced by means of an incision essentially perpendicular to the existing incision and penetrating the latter.

For this purpose, a ring-shaped flap incision is made, essentially concentric to the existing incision, which extends all the way to the required diameter and the inside diameter of which is less than the existing incision diameter. Even in the case of slight lateral decentering of the two incisions, an overlap is always produced. In the same work step (without repositioning of the eye), an almost complete lateral incision is made from the outside diameter of the ring-shaped incision all the way to the front of the cornea. In this connection, no incision is made over an angle range where the hinge is supposed to be formed. Also in the same work step, a defined connection is produced between the ring-shaped incision and the existing incision, in that a completely circumferential mantle incision, which links with the inside diameter of the ring-shaped incision, is made between the depth of the new incision (which can be deeper or less deep than the existing incision) and a second depth. In this connection, the second depth is selected in such a manner that the mantle incision intersects all the probable depths of the existing incision, including depth tolerances.

A method according to an embodiment of the invention, for expansion of existing incisions in the corneal tissue, using a fs laser, may be characterized in that:
  the edge 404 of the existing incision 301 lies in a probable region 405 relative to an expanding incision to be introduced,
  the expanding incision 302 to be newly introduced overlaps the probable region 405 completely, over a length 401 parallel to the existing incision,
  the expanding incision 302 to be newly introduced overlaps the probable region 405 completely, over a width 403 perpendicular to the existing incision,
  the expanding incision 302 to be newly introduced is cohesive in the overlap region for length and width, and thereby is guaranteed to penetrate the end of the existing incision, as long as the latter is situated in the probable region 405.

In this connection, the incision surfaces penetrate one another at the connection location between the incision surfaces of the existing incision 301 and of the expanding incision 302 to be performed, at a steep angle (30°-150°) or (45°-135°) or (60°-120°) or (85°-95°), respectively.

A minimum distance 402 from the existing incision is maintained between the existing incision 301 and the expansion incision 302 outside of the overlap region 401.

In this connection, the vertical overlap region 403 is selected in such a manner that it corresponds to the greatest probable deviation in the positioning of the expanding incision 302 relative to the existing incision 301 in the direction essentially perpendicular to the existing incision 301.

In this connection, the distance 402 is selected in such a manner that it exceeds the greatest probable deviation in the positioning of the expanding incision 302 relative to the existing incision 301 in the direction essentially perpendicular to the existing incision 301.

In this connection, the overlap region 401 is selected in such a manner that it corresponds to the greatest probable deviation in the positioning of the expanding incision 302 relative to the existing incision in the direction essentially perpendicular to the existing incision 301.

In this connection, the sizes of the regions 401 and 403 are derived from known positioning tolerances of the fs laser system.

The method for expansion of a circular flap incision in the cornea, in which the incision for expansion consists of the elements: 1) connection, b) expansion ring, c) opening, which are characterized in that the connection 306 penetrates the existing incision 301 in the manner described above, the expansion ring 201, 302 follows the connection 202, 306 without a gap and extends further in the flap direction than the existing incision 100, 301, but has a defined distance perpendicular from the existing incision, and the opening 202 follows the expansion ring 201, 302 without a gap and leads to the cornea surface 17.

In this connection, the opening can be interrupted by a hinge, so that the cornea part 120 is not detached above the existing incision and the expanding incision, but rather remains attached on one side in hinge-like manner.

In this connection, the connection 306 can also follow the expansion incision 302 on both sides (in T shape toward the top and the bottom).

The data for the partial incisions 302 and 306 determined in this way are provided to the planning device 16, which generates the control data required for appropriate control of the laser from them.

The particular advantage of the invention consists in that a flap is cut for expansion of a refractive treatment according to the SMILE method, as in the Flex method, and further treatment is conducted according to the latter method.

In addition, it should still be noted that of course, the treatment apparatus 1 or the planning device 16, respectively, also allows concrete implementation of the method explained above in general terms.

A further embodiment of the planning device exists in the form of a computer program or of a corresponding data medium with a computer program, which implements the planning device on a corresponding computer, so that input of the measurement data to the computer takes place by way of suitable data transmission means, and the control data are transmitted from this computer to the control device 11, for which purpose, once again, data transmission means known to a person skilled in the art can be used.

The invention claimed is:

1. A planning device for generating control data for a treatment apparatus for ophthalmic surgery, which cuts at least one incision surface in a cornea, using a laser device, the planning device including:

a calculation device comprising a computer configured to receive data of a previously-introduced cornea incision surface having an existing flap incision and an existing opening incision extending from an exterior surface of the cornea to the existing flap incision so as to form at least a partial existing corneal flap, and to establish a new cornea incision surface, based on the data of the previously-introduced cornea incision surface and to generate a control data set for controlling the laser device for the new cornea incision surface, wherein the computer of the calculation device is further configured to determine the new cornea incision surface having a new flap incision that is ring-shaped and located posterior to the existing flap incision, a new opening incision located lateral to the existing flap incision and extending from the exterior surface of the cornea to the new flap incision, and a connecting mantle incision connecting the new flap incision to the existing flap incision in such a manner that the existing flap incision of the previously-introduced cornea incision surface is intersected by at least a part of the connecting mantle incision of the new cornea incision surface at an angle between 60° and 120°, such that a new hinged corneal flap is formed, the new hinged corneal flap including portions of the at least partial existing corneal flap.

2. The device according to claim 1, wherein the calculation device establishes the new cornea incision surface as a continuation of the previously-introduced cornea incision surface, wherein an overlap region is provided between the previously-introduced cornea incision surface and the new cornea incision surface.

3. The device according to claim 1, wherein the information concerning the previously-introduced cornea incision surface comprises data generated during a previous operation or data generated directly subsequent to a previous operation, and which enables reproduction of a location and shape of the previously-introduced cornea incision surface.

4. A treatment apparatus for ophthalmic surgery, comprising a laser device that cuts at least one incision surface in the cornea by means of laser radiation in accordance with control data, and the planning device for generating the control data according to claim 1.

5. The apparatus according to claim 4 further comprising a device for recording progression of a production of the new cornea incision surface.

6. The apparatus according to claim 4, wherein the laser device emits focused, pulsed laser radiation into the cornea and produces an incision by adjusting a focus position along an incision surface.

7. The planning device of claim 1, wherein the existing flap incision of the previously-introduced cornea incision surface is intersected by at least a part of the connecting mantle incision of the new cornea incision surface at an angle between 80° and 100°.

8. The planning device of claim 7, wherein the existing flap incision of the previously-introduced cornea incision surface is intersected by at least a part of the connecting mantle incision of the new cornea incision surface at an angle of approximately 90°.

9. The planning device of claim 1, wherein the computer is further configured to establish the new cornea incision surface, to generate the control data set, and to determine the new cornea incision surface in the manner that the existing flap incision of the previously-introduced cornea incision surface is intersected by at least a part of the connecting mantle incision of the new cornea incision surface at an angle between 60° and 120°.

10. A method for generating control data for a treatment apparatus for ophthalmic surgery which cuts at least one incision surface in the cornea using a laser device, the method comprising:

making available cornea data that contain information about a cornea incision surface that has been previously introduced, the previously-introduced cornea incision surface having an existing flap incision and an existing opening incision extending from an exterior surface of the cornea to the existing flap incision so as to form at least a partial existing corneal flap, establishing a new cornea incision surface based on the cornea data, the new cornea incision surface having a new flap incision that is ring-shaped and located posterior to the existing flap incision, a new opening incision located lateral to the existing flap incision and extending from the exterior surface of the cornea to the new flap incision, and a connecting mantle incision connecting the new flap incision to the existing flap incision, and generating a control data set for the new cornea incision surface for controlling the laser device, wherein the new cornea incision surface is determined in such a manner that the existing flap incision of the previously-introduced cornea incision surface is intersected by at least a part of the connecting mantle incision of the new cornea incision surface at an angle between 60° and 120°, such that a new hinged corneal flap is formed, the new hinged corneal flap including portions of the at least partial existing corneal flap.

11. The method of claim 10, wherein the existing flap incision of the previously-introduced cornea incision surface is intersected by at least a part of the connecting mantle incision of the new cornea incision surface at an angle between 80° and 100°.

12. The method of claim 11, wherein the existing flap incision of the previously-introduced cornea incision surface is intersected by at least a part of the connecting mantle incision of the new cornea incision surface at an angle of approximately 90°.

13. A method for ophthalmic surgery, wherein at least one incision surface in a cornea is cut with a laser device using a treatment apparatus, wherein the method comprises:

making available cornea data that contain information about a cornea incision surface that has been previously-introduced, the previously-introduced cornea incision surface having an existing flap incision and an existing opening incision extending from an exterior surface of the cornea to the existing flap incision so as to form at least a partial existing corneal flap, establishing a new cornea incision surface based on the cornea data, the new cornea incision surface having a new flap incision that is ring-shaped and located posterior to the existing flap incision, a new opening incision located lateral to the existing flap incision and extending from the exterior surface of the cornea to the new flap incision, and a connecting mantle incision connecting the new flap incision to the existing flap incision, and generating a control data set for the new cornea incision surface, transmitting the control data to the treatment apparatus, and producing the new cornea incision surface by controlling the laser device with the control data set, wherein the new cornea incision surface is determined in such manner that the existing flap incision of the previously-introduced cornea incision surface is intersected by at least a part of the connecting mantle incision of the new cornea incision surface at an angle between 60° and 120°, such that a new hinged corneal flap is formed, the new hinged corneal flap including portions of the at least partial existing corneal flap.

14. The method according to claim 13, wherein the new cornea incision surface continues incisions previously made, wherein an overlap region is provided between the previously-introduced incision surface and the new cornea incision surface.

15. The method according to claim 14, wherein a progression of production of the new cornea incision surface is recorded.

16. A tangible computer readable data medium storing a computer program product having program code that performs the method according to claim 13.

17. The method of claim 13, wherein the existing flap incision of the previously-introduced cornea incision surface is intersected by at least a part of the connecting mantle incision of the new cornea incision surface at an angle between 80° and 100°.

18. The method of claim 13, wherein the existing flap incision of the previously-introduced cornea incision surface is intersected by at least a part of the connecting mantle incision of the new cornea incision surface at an angle of approximately 90°.

* * * * *